(12) United States Patent
Greiser

(10) Patent No.: US 8,581,583 B2
(45) Date of Patent: Nov. 12, 2013

(54) METHOD AND APPARATUS FOR MAGNETIC RESONANCE IMAGING TO CREATE T1 MAPS

(75) Inventor: Andreas Greiser, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 384 days.

(21) Appl. No.: 13/011,122

(22) Filed: Jan. 21, 2011

(65) Prior Publication Data

US 2011/0181285 A1    Jul. 28, 2011

(30) Foreign Application Priority Data

Jan. 22, 2010    (DE) .................. 10 2010 001 145

(51) Int. Cl.
  *G01V 3/00*    (2006.01)
(52) U.S. Cl.
  USPC .......................................... 324/309; 324/307
(58) Field of Classification Search
  USPC .................................. 324/309, 307, 306, 314
  See application file for complete search history.

(56) References Cited

U.S. PATENT DOCUMENTS

| | | | | |
|---|---|---|---|---|
| 6,803,762 B2 * | 10/2004 | Shah et al. | ..................... | 324/309 |
| 7,071,689 B2 * | 7/2006 | Golay et al. | ................... | 324/309 |
| 7,276,904 B2 * | 10/2007 | Busse et al. | ................... | 324/309 |
| 7,443,162 B2 * | 10/2008 | Deimling | ...................... | 324/307 |
| 2008/0004518 A1 * | 1/2008 | Stehning et al. | ............. | 600/410 |

OTHER PUBLICATIONS

"A New Method for Fast Quantitative Mapping of Absolute Water Content In Vivo," Neeb et al., NeuroImage, vol. 31 (2006) pp. 1156-1168.
"Phase-Encoding Strategies for Optimal Spatial Resolution and $T_1$ Accuracy in 3D Look-Locker Imaging," Nkongchu et al., Magnetic Resonance Imaging, vol. 25 (2007) pp. 1203-1214.
"Development and Validation of a Novel Method for Transferring Input Function Signal Intensity to [Gd-DTPA] for Quantitative Assessment of Myocardial Perfusion," Fischer et al., Proc. Intl. Soc. Mag. Reson. Med., vol. 2 (1997).
"Modified Look-Locker Inversion Recovery (MOLLI) for High-Resolution $T_1$ Mapping of the Heart," Messroghli et al., Magnetic Resonance in Medicine, vol. 52 (2004) pp. 141-146.

* cited by examiner

*Primary Examiner* — Louis Arana
(74) *Attorney, Agent, or Firm* — Schiff Hardin LLP

(57) ABSTRACT

In a method and apparatus for MR imaging, a data acquisition sequence is executed wherein at least two slices of an examination subject are imaged in parallel with a gradient echo method for spatially resolved quantification of the T1 relaxation time. At least one first acquisition sequence is implemented to acquire MR data from a first slice of the examination subject and at least one second acquisition sequence is implemented to acquire MR data from a second slice of the examination subject. The acquisition sequences each include an inversion pulse and at least two successive readout steps. The first and second acquisition sequences are temporally offset from one another such that they at least partially overlap.

25 Claims, 6 Drawing Sheets

METHOD AND APPARATUS FOR MAGNETIC RESONANCE IMAGING TO CREATE T1 MAPS

BACKGROUND OF THE INVENTION

1. Field of the Invention

The present invention concerns a method for magnetic resonance (MR) imaging in which a spatially resolved quantification of the T1 relaxation time is created with a gradient echo method. The invention furthermore concerns a magnetic resonance system to implement such a method.

2. Description of the Prior Art

Magnetic resonance tomography (MRT) is an examination modality with which regions inside an examination subject can be shown with high resolution and good contrast, in particular even soft tissues such as muscles and organs. A dependency of the measured MR signal on the T1 and T2 relaxation times can be achieved by appropriate acquisition sequences. The relaxation times T1 and T2 are the time constants of the decay of the macroscopic magnetization excited in the tissue, which vary for different tissues. The spin lattice relaxation time T1 is characteristic of a process that produces the reestablishment of the longitudinal steady state magnetization that appears in an applied basic magnetic field $B_0$.

For example, conventional methods use T1-weighted "delay enhancement" methods in order to characterize the tissue state of the cardiac muscle (myocardium). Such methods provide a high tissue contrast and are presently the standard in the determination of the local vitality. However, these methods are not quantitative, meaning that they merely enable a delimitation between healthy and destroyed tissue but not a differentiation in the transition range or in ischemic but not infracted tissue regions.

Such a quantification could be achieved with a quantitative, per pixel representation of the T1 time since this is a measurement-independent variable and enables the subdivision of the tissue into regions with varying T1 values. However, conventional methods for T1 quantification can not be used to depict the cardiac muscle because heart beat and breathing movement prevent an artifact-free depiction.

The MOLLI (Modified Look-Locker Inversion Recovery) method is known in order to quantify the T1 relaxation time in the myocardium. The method is based on an inversion recovery method in which the steady state magnetization is inverted by means of a 180° pulse. Measurements along the T1 decay curve are then conducted with subsequent readout steps. The MOLLI method has the advantage that all necessary data can be acquired within a breath hold phase in order to generate a T1 map for an imaging slice. Due to the properties of the single shot readout steps that are used, the method is subject to limitations with regard to the possible temporal and spatial resolution. In particular, the method enables the acquisition of only one slice so that a volumetric coverage of the heart during a breath hold phase is not possible with the MOLLI acquisition scheme. The measurement of an additional slice in a second breath hold phase is advantageous since in the meantime a movement of the examination subject has most likely occurred, such that sequentially acquired slices exhibit movement artifacts and cannot be directly associated with one another for volumetric presentation.

SUMMARY OF THE INVENTION

An object of the present invention is to provide an improved method for spatially resolved quantification of the T1 relaxation time that in particular is suitable for volumetric scanning and generation of a T1 map, for example of a beating heart.

According to the present invention, this object is achieved by a method for MR imaging in which, with a pulse sequence, at least two slices of an examination subject are imaged in parallel with a gradient echo method for spatially resolved quantification of the T1 relaxation time. The method includes the implementation of at least one first acquisition sequence for acquisition of MR data from a first slice of the examination subject and the implementation of at least one second acquisition sequence to acquire MR data from a second slice of the examination subject, the acquisition sequences respectively including an inversion pulse and at least two successive readout steps. The first and second acquisition sequences are temporally offset from one another such that they at least partially overlap.

Multiple slices can be scanned within a breath hold phase through the parallel imaging of at least two slices of the examination subject, such that a volumetric representation is enabled. The overlap of the first and second acquisition sequences can amount to at least 50% or advantageously can be greater than 70% or 80% of the respective acquisition sequence. Acquisition of multiple slices within a short time period is therefore possible.

In an embodiment of the present invention, the inversion pulses of the acquisition sequences are slice-selective. For example, by application of a slice selection gradient they can be radiated such that a slice-selective inversion of the magnetization takes place. The decay of the excited, macroscopic magnetization thus can be observed in parallel in multiple slices.

An MR image of the corresponding slice of the examination subject can be acquired with each readout step. The readout step can thus comprise a single shot sequence so that MR images can be acquired at different points in time of the T1 decay curve.

The acquisition sequences are advantageously T1-weighted, wherein the corresponding readout steps for scanning the decay curve of the magnetization excited by the inversion pulse are designed in order to determine the T1 relaxation time. Each readout step therefore scans a different point on the T1 decay curve, i.e. the time curve of the decay of the excited magnetization.

It is advantageous to configure the readout step such that a transverse magnetization that is present before the implementation of the readout step—which transverse magnetization is caused by the inversion pulse in the respective slice—is rephased again after the implementation of the readout step. The readout thus advantageously takes place with a sequence in which the gradients compensate in every spatial direction, i.e. with what is known as a "balanced" sequence. In particular, every readout step can be a True FISP (True Fast Imaging with Steady State Precision) sequence or a b-SSFP (Balanced Steady State Free Precision) sequence. It is thereby enabled to track the decay of the steady state magnetization that is deflected by the inversion pulse with multiple sequential readout steps.

The readout steps can furthermore include a parallel imaging method in which only one part of k-space is scanned to acquire an MR image. K-space can then be filled based on additional information that, for example, is acquired with an external reference scan preceding the acquisition scheme. Examples of parallel imaging methods that can be used are GRAPPA (generalized autocalibrating partially parallel acquisition) and SENSE (sensitivity encoding).

The time offset between the acquisition sequences for different slices can be set such that the inversion pulse and the readout steps of the at least one acquisition sequence for the first slice do not temporally intersect with the inversion pulse and the readout steps of the at least one acquisition sequence for the second slice. The acquisition sequences can thus be implemented in parallel without a mutual influencing or interference occurring.

Naturally it is also possible to implement at least one third acquisition sequence for at least one additional third step, which at least one third acquisition sequence temporally overlaps with the first and/or second acquisition sequence such that the inversion pulse and the readout steps of the third acquisition sequence do not temporally intersect with those of the first and second acquisition sequences. Insofar as such intersections are avoided, MR data can also be acquired in parallel for additional slices.

According to a further embodiment, the implementation of the acquisition sequences is triggered at the heart beat of the examination subject. For example, a cardiac cycle of the heart of the examination subject can include varying cardiac phases, wherein the trigger event is generated in a specific cardiac phase. An EKG can be used for the triggering, with the triggering taking place at the R-spike, for example; however, self-triggering on the basis of acquired MR data and other triggering methods are also conceivable.

The readout steps of each acquisition sequence are advantageously implemented in the same respective phase of successive cardiac cycles. For example, the readout steps are implemented a specific, fixed time period after the trigger event. It is thus ensured that the MR images acquired for the slice originate from the same cardiac phases.

Furthermore, the time offset can be set such that the inversion pulses of the first and second acquisition sequence are radiated at different cardiac phases during the same cardiac cycle. The acquisition sequences can thus be started during the same cardiac cycle without the inversion pulses temporally intersecting. In particular, the first and second acquisition sequences can be implemented during the same cardiac cycles. This means that they can start in the same cardiac cycle and exhibit the same number of readout steps. The acquisition sequences for additional slices to be scanned in parallel can naturally be similarly configured.

The offset can also be set such that the readout steps of the first and second acquisition sequence are implemented at different cardiac phases. A temporal intersection of the readout steps executed in parallel can thus be avoided. "Cardiac phase" relates to a specific point in time of the cardiac cycle, for example a specific time after the occurrence of the trigger event. For example, the readout steps for the different slices can be implemented during the late diastole of the cardiac cycle. The cardiac cycle in which the inversion pulse is radiated can also already comprise a readout step.

In a further embodiment, at least two—advantageously at least three—acquisition sequences are implemented for each slice. A sufficient set of MR data can therefore be acquired for a precise determination of the T1 relaxation time.

A recovery time period (recovery period) can follow each acquisition sequence, which recovery period includes a specific number of cardiac cycles (recovery heart beats), for example. After the last acquisition sequence such a thing is naturally no longer required.

Furthermore, an "interleaved" acquisition can take place. The first slice and the second slice can belong to a first group of slices and respectively be scanned with at least two acquisition sequences, wherein a recovery period follows each acquisition sequence. At least one additional slice can then be scanned with at least one additional acquisition sequence that is implemented during the recovery periods between the acquisition sequences for the slices of the first group. The recovery period for the slices of the first group comprises the same recovery heart beats during which the acquisition sequence for the additional slice is implemented, for example.

Naturally, additional slices can also be scanned in parallel during the recovery. The additional slice can belong to a second group of slices that are scanned with temporally overlapping acquisition sequences, wherein the acquisition sequences for the slices of the second group are implemented during the recovery periods between the acquisition sequences for the slices of the first group. A number of slices—for example at least six—can thus be acquired during one breath hold phase via parallel scanning of multiple slices and utilization of the recovery heart beats. It can be advantageous if adjacent slices are associated with different groups so that slices scanned in parallel have a greater spatial separation from one another.

In an additional embodiment, at most two acquisition sequences are implemented for each slice, wherein the at most two acquisition sequences together comprise not more than six (advantageously not more than five) readout steps. An additional acceleration of the method can be achieved via a limitation of the acquisition sequences and readout steps, such that additional slices can be acquired during a breath hold phase. A precise determination of the T1 relaxation time can also thereby already take place with five readout steps.

The sequence scheme is advantageously implemented during a breath hold phase of the examination subject. Movement artifacts in a volumetric imaging can thereby be avoided by parallel scanning of multiple slices.

The method can furthermore comprise the determination of the T1 decay time to create a T1 map for a slice from the MR data acquired for the slice. In particular, an MR image can be reconstructed from the MR data acquired with each readout sequence, wherein a T1 relaxation time is determined by means of a statistical method for each pixel from the MR images reconstructed for a slice. For example, a curve adaptation to the intensity values of the same pixel can take place in the various MR images (for example using the method of least square error). The T1 time can therefore be determined precisely.

Furthermore, it is advantageous to implement the acquisition sequences in a magnetic field strength of at least 2.5 Tesla, advantageously 3 Tesla. A higher signal-to-noise ratio (SNR) can thereby be achieved.

Naturally, it is not only a first and second slice that can be scanned with the method described in the preceding, but also the parallel acquisition of a third or further slices is likewise possible, with the cited method steps being applied accordingly to the acquisition sequences for the additional slices. For example, three slices can be scanned in parallel with two or more acquisition sequences respectively, wherein three additional slices are likewise scanned in parallel during the recovery periods of the first cited slices. For example, six slices can thus be acquired during a single breath hold phase.

According to a further aspect of the present invention, a magnetic resonance system is provided that is designed to implement a data acquisition procedure in which at least two slices of an examination subject are imaged in parallel with a gradient echo method for spatially resolved quantification of the T1 relaxation time. The magnetic resonance system has an acquisition unit that is designed to radiate RF pulses into the examination subject and to acquire MR data from the examination subject, and a control unit. The control unit is designed in order to activate the acquisition unit to implement the following steps: implement at least one first acquisition sequence to acquire MR data from a first slice of the examination subject; and implement at least one second acquisition sequence to acquire MR data from a second slice of the examination subject; wherein the acquisition sequences respectively include an inversion pulse and at least two successive readout steps, and wherein the first and second acquisition sequence are temporally offset from one another such that they at least partially overlap.

Advantages similar to those described in the preceding can be achieved with the magnetic resonance system according to the invention. Furthermore, the magnetic resonance system can be designed to implement any of the embodiments of the method described in the preceding. In particular, the control unit can initiate the implementation of the acquisition sequences with such a time offset that the inversion pulse and the readout steps of the acquisition sequence for one slice do not temporally intersect with the inversion pulse and the readout steps of an acquisition sequence for another slice.

The features of the embodiment described in the preceding and in the following can naturally be combined with one another.

DESCRIPTION OF THE PREFERRED EMBODIMENTS

Figure 1:
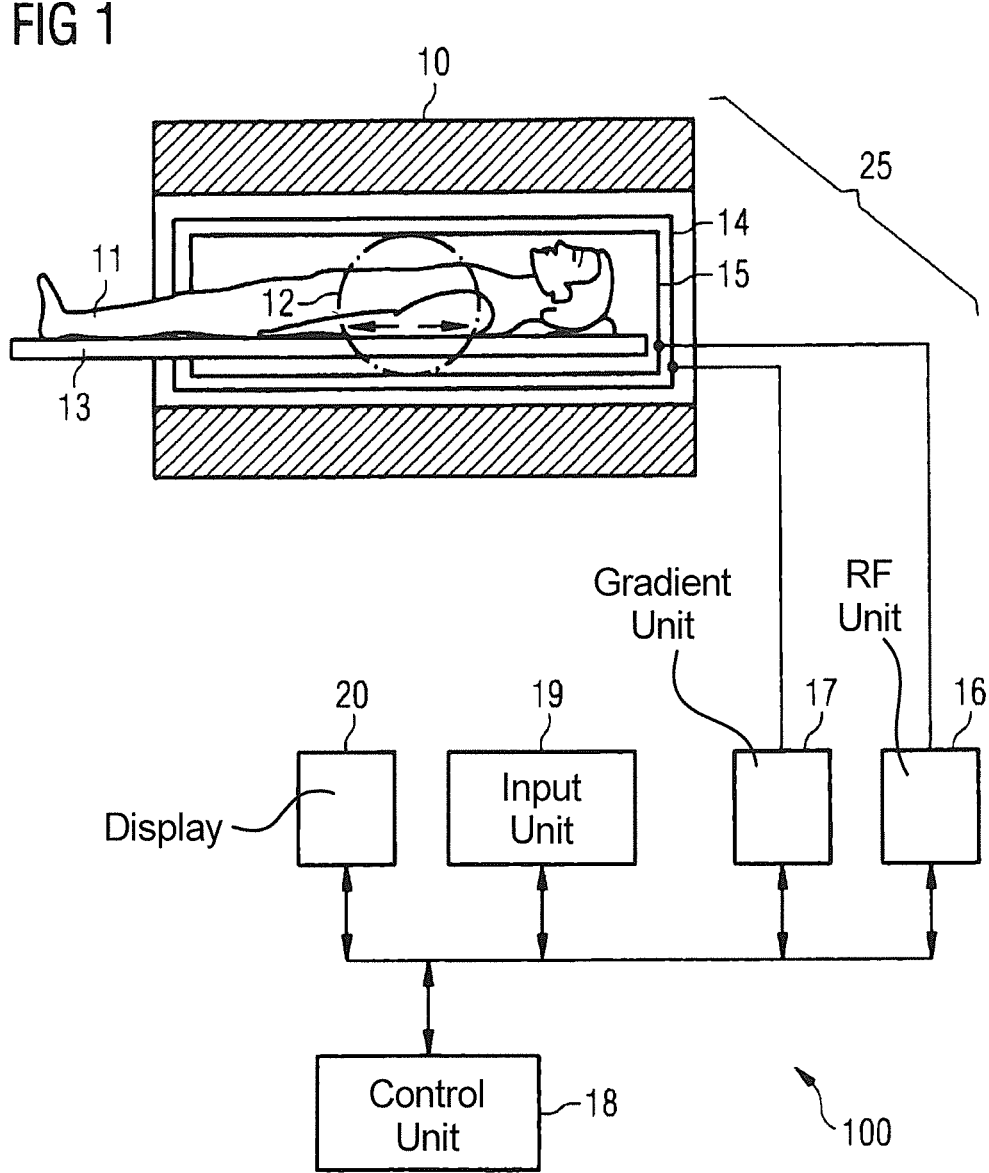
FIG. 1 schematically shows an embodiment of the magnetic resonance system according to the invention.

FIG. 1 schematically shows a magnetic resonance system 100 which is designed to implement acquisition sequences for spatially resolved quantification of T1 relaxation times in parallel. Such a magnetic resonance system possesses a magnet 10 to generate a polarization field B0. To increase the signal-to-noise ratio, field strengths of at least 2.5 T (advantageously 3.0 T) can thereby be used. An examination subject (here an examined person 11) on a bed table 13 can be slid into the magnet, as is schematically depicted by the arrows. The MR system furthermore possesses a gradient system 14 to generate magnetic field gradients that are used for the imaging and spatial coding. To excite the polarization resulting in the basic magnetic field, a radio-frequency coil arrangement 15 is provided that radiates a radio-frequency (RF) field into the examined person 11 in order to deflect the magnetization out of the steady state. A gradient unit 17 is provided to control the magnetic field gradients and an RF unit 16 is provided to control the radiated RF pulses.

In particular, RF pulses with variable flip angle can be radiated by means of the RF unit. For example, a 180° inversion pulse to invert the excited magnetization and pulses with a flip angle smaller than 90° can be radiated, for example in the implementation of a readout step with a True FISP sequence. The RF coil arrangement 15 can be used to acquire magnetic resonance signals from the examination region 12. However, additional acquisition coils or component coils can be used, in particular given the utilization of a parallel imaging method such as GRAPPA or SENSE. A larger coil array can likewise be provided that comprises 3, 6, 32 or more coils, for example. Due to the spatially independent arrangement of the coils, additional spatial information is obtained that can be used in order to achieve an additional spatial coding via the combination of the magnetic resonance signals acquired simultaneously by the multiple coils. For example, this can be achieved by means of the sensitivity profiles of the respective coils, for which the profiles are measured or otherwise determined. Based on this additional spatial information it is enabled that it is not necessary to respectively scan the entirety of k-space in the readout steps in order to acquire MR images. For example, k-space lines can be skipped that are subsequently reconstructed with the additional information. Parallel imaging methods such as GRAPPA and SENSE are known to those skilled in the art, such that a more detailed description is not necessary herein.

The components to radiate RF pulses and to receive MR signals (for example the units 14-17) can also be designated as an acquisition unit 25. The magnetic resonance system 100 is centrally controlled by a control unit 18. For example, this can initiate the implementation of a defined sequence scheme. Control information (for example imaging parameters) and reconstructed MR images can be displayed on the display 20. A selection of the sequence scheme to be implemented as well as an adjustment of imaging parameters or other operating parameters can take place via the input unit 19. Among other things, with the input unit 19 the slices can be selected that should be scanned in parallel with an embodiment of the method according to the invention during a breath hold phase of the examined person 11.

Control unit 18 can furthermore include a computer or evaluation unit that evaluates acquired MR signals or, respectively, MR data. On the one hand, image data can thereby be reconstructed from the raw MR data by means of a Fourier transformation; on the other hand, the T1 relaxation time can be determined with spatial resolution from a series of MR images that were taken of a slice. In particular, the magnetic resonance system 100 is configured to implement the method described in the following.

Furthermore, a device can be provided for EKG triggering (not shown). This registers the electrical activity of the heart muscle, for example to acquire an electrocardiogram (EKG). Multiple electrodes are thereby arranged on the examined person 11. An acquisition sequence to acquire MR data can then be triggered—for example at the R-spike of the acquired EKG—so that multiple readout steps of the acquisition sequence are respectively implemented in the same phase of the cardiac cycle, for example a predetermined time period after the occurrence of the respective trigger event. Acquisition sequences for parallel scanning of multiple slices can be offset in time by means of such a triggering so that the readout steps do not temporally intersect. The configuration is explained in detail in the following. In other embodiments, a cardiac triggering can take place without using an electrocardiogram, for example by means of a self-triggering based on acquired MR data.

The magnetic resonance system 100 can naturally comprise additional components that conventional magnetic resonance systems customarily have. The general mode of operation of a magnetic resonance system is known to those skilled in the art, so a more detailed description of the general components is not necessary herein.

Figure 2:
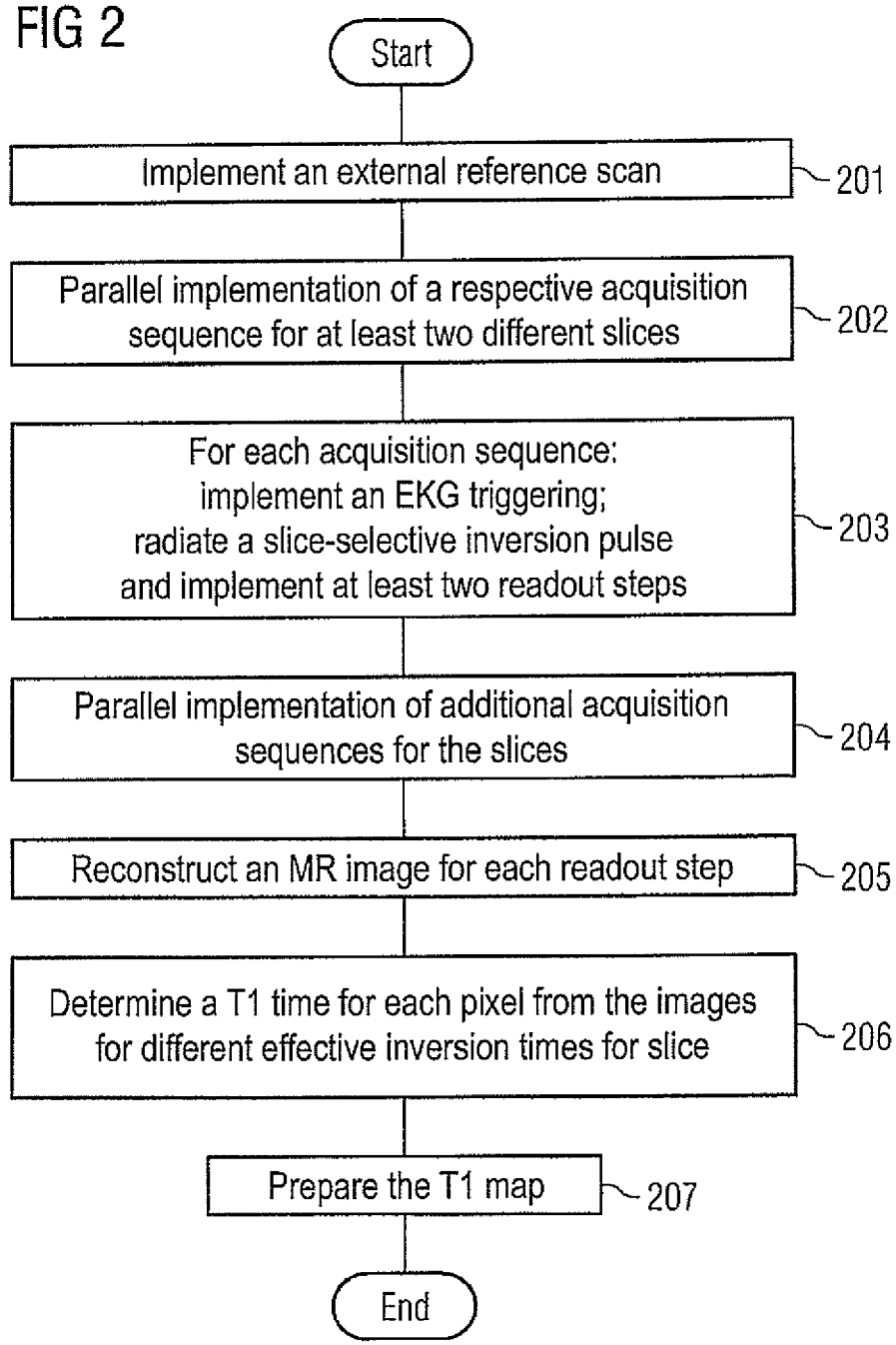
FIG. 2 schematically shows a flow diagram of an embodiment of the method according to the invention.
Figure 3:
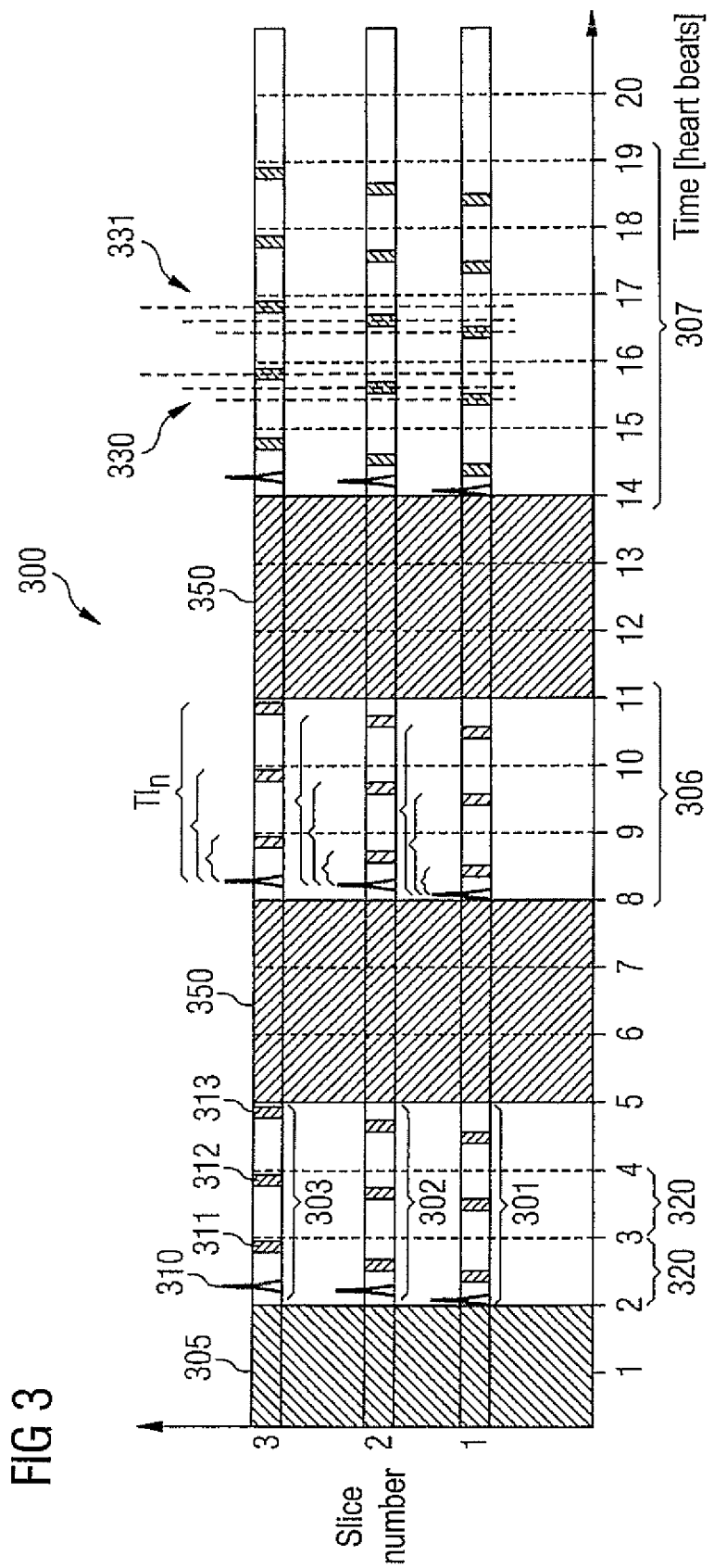
FIG. 3 schematically illustrates a sequence scheme according to one embodiment of the present invention in which three slices are scanned in parallel.

FIG. 2 shows a flow diagram of a method according to one embodiment of the present invention that can be implemented with the magnetic resonance system 100. In Step 201 an external reference scan is initially conducted that, for example, serves for the acquisition of the additional spatial information or, sensitivity information of the acquisition coils. In FIG. 3 the reference scan is indicated with the reference character 305. It enables the use of a parallel imaging method such as GRAPPA or SENSE so that only a portion of k-space must be scanned in subsequent readout steps.

A parallel implementation per acquisition sequence takes place in Step 202 for at least two different slices. Three slices (1, 2, 3) are scanned in parallel with the sequence scheme 300 that is illustrated in FIG. 3. For this the three acquisition sequences 301, 302 and 303 are implemented in parallel with a slight time offset.

For each acquisition sequence the implementation of an EKG triggering, the radiation of a slice-selective inversion pulse and the implementation of at least two readout steps (FIG. 2, Step 203) takes place. The time offset between the acquisition sequences 301, 302 and 303 can be set by means of the EKG triggering. This ensures that the sequential readout steps 311, 312 and 313 are always executed at the same phase of a cardiac cycle 320, namely a predetermined time period after the trigger event. Moreover, by suitable selection of the time periods for the different slices it can be ensured that the readout steps of the acquisition sequences 301, 302 and 303 do not temporally intersect. In FIG. 3 this is illustrated for two successive cardiac cycles by means of the line groups 330 and 331. The RF pulses to be radiated and MR signals to be acquired in the readout steps can thus be uniquely associated with a specific slice.

By means of the slice-selective inversion pulses 310 that are radiated in each acquisition sequence, the steady state magnetization is inverted only in the respective slice. Moreover, the inversion time for the respective slice can be set independently. As shown in FIG. 3, the inversion pulses for the slices to be scanned in parallel are advantageously radiated during the same cardiac cycle but at different points in time or, respectively, phases of the cardiac cycle. The acquisition sequences 301-303 each include three readout steps 311-313, wherein the first readout step already takes place in the cardiac cycle in which the inversion pulse is radiated.

For each readout step 311-313 a True FISP sequence (which is also called a balanced SSFP sequence) is implemented. This represents a variant of the Fast Low Angle Shot (FLASH) sequence in which the gradients that are shifted during the acquisition of the MR signals mutually compensate in each spatial direction. True FISP is a single shot sequence in which an entire MR image is acquired. An MR image of the respective slice is thus acquired with each readout step 311, 312 and 313.

The True FISP sequence enables exposures with high contrast to be created with short repetition times (and thus short acquisition times). The sequence is normally symmetrical in structure and comprises an α-pulse (with the flip angle α) during the radiation of which a slice selection gradient is applied as well as the application of a read gradient and phase coding gradients. For dephasing of the magnetization the read gradient is initially switched in an inverted manner, wherein the magnetization rephrases at the subsequently applied read gradient and a corresponding gradient echo signal is thereby caused that can finally be acquired. The same gradients may be subsequently shifted with inverted polarity so that the gradient moments of the sequence compensate and the radiation of a −α pulse takes place. At the end of the sequence interval the gradients are therefore compensated in every spatial direction and the transversal magnetization is again in phase at the point in time of the following excitation pulse. The sequence interval can be implemented for multiple phase coding steps so that a complete MR image of the respective slice is obtained in a readout step. Frequency and phase can be evaluated from the acquired MR signals. As already mentioned, given the use of parallel imaging methods not every k-space line must be scanned with a phase coding step; rather, the missing k-space lines can be supplemented with additional spatial information that can be obtained with a component coil array, for example. The parallel imaging methods sigh as GRAPPA or SENSE therefore accelerate the implementation of the readout steps by the reduction of the necessary phase coding steps. For example, a readout step can exhibit a duration of only 100-200 ms. Naturally, in the method according to the invention it is likewise conceivable to use other single shot acquisition sequences that enable the acquisition of an MR image with variable flip angle within a short time period.

Each acquisition sequence with its readout steps thereby essentially corresponds to a Look-Locker experiment. In this the time curve of the decay of the inverse magnetization appearing after the inversion pulse is scanned. The inversion pulse prepares the longitudinal magnetization that then relaxes exponentially with the time constant T1, and in fact into the steady state magnetization predetermined by the B0 field. The readout steps scan this decay by deflecting a transversal component of the magnetization with a limited flip angle. The MR signals acquired with the readout steps therefore represent a set of measurements along the T1 decay curve. For example, the T1 relaxation time can be determined from these measurements with the method of least square error. At each readout step the relaxation of the magnetization has progressed further, such that a different point in time of the decay curve is scanned accordingly.

In the present embodiment, the readout steps 311-313 of each readout sequence 301-303 respectively occur in the same phase of the cardiac cycle 320. In order to determine the T1 times with high precision, additional groups of parallel acquisition sequences 306 and 306 can subsequently be implemented. Different inversion times are thereby advantageously used so that different points in time along the T1 decay curve are scanned than were scanned with the preceding acquisition sequences 301-303. The inversion times $TI_n$ are schematically illustrated by the curly brackets for the acquisition sequences 306 in FIG. 3. The inversion time is thereby defined by the time interval from the middle of the inversion pulse to the middle of the respective readout step, for example. The use of slice-selective inversion pulses enables the inversion times to be set independently for each slice to be scanned. A high flexibility in the selection of the points of the T1 decay curve that are to be scanned is therefore achieved for each slice.

In the example of FIG. 3, three successive acquisition sequences are implemented for each slice, wherein the first two acquisition sequences respectively possess three readout steps and the third acquisition sequence respectively possesses five readout steps. The MR data or, respectively, MR images acquired with the readout steps can subsequently be assembled into a common data set so that a high precision of the determination of the T1 relaxation time can be achieved with the corresponding statistical method. The readout steps of the subsequent acquisition sequences of the same slice can thereby also be implemented in the same cardiac phase.

The parallel implementation of additional acquisition sequences 306 and 307 for the slices to be scanned is illustrated in Step 204 in FIG. 2. The reconstruction of an MR image for each readout step subsequently takes place for each slice in Step 205. A supplementation of k-space according to one of the parallel imaging methods described in the preceding can initially take place for this, whereupon image data are obtained from the raw k-space data by means of a 2D Fourier transformation. These image data for each slice are subsequently evaluated in Step 206. The determination of a T1 relaxation time for each pixel from the images that were acquired for each slice for the different effective inversion times thereby takes place. In the example of FIG. 3, eleven intensity values for different inversion times are provided for each pixel from the eleven readout steps. A corresponding decay curve can be adapted to this time curve of the intensity values in order to determine the T1 time constants for the pixel. This takes place for all pixels of the image format so that a spatially resolved representation of the T1 relaxation time is enabled; what is called a T1 map is thus obtained. Naturally, it is not necessary to evaluate every single pixel; the T1 relaxation time can also be evaluated only in regions of interest. Since eleven measurement values are provided for the curve adaptation (thus the adaptation equation is overdetermined), T1 can be determined with high precision.

The creation of the T1 map takes place in Step 207. In the example illustrated in FIG. 3, the data to create the T1 map are acquired for three slices in parallel within 19 heart beats or, respectively, cardiac cycles. The acquisition scheme can thereby be implemented within one breath hold phase of the examined person.

Movement artifacts that would be unavoidable given a sequential scanning of the various slices can thus be significantly reduced. In the embodiment of FIG. 3, the T1 relaxation time in a breath hold phase can be quantified simultaneously, with spatial resolution, for three slices. A volumetric representation of the T1 times, for example for the heart, can therefore be realized with significantly reduced movement artifacts.

Figure 4:
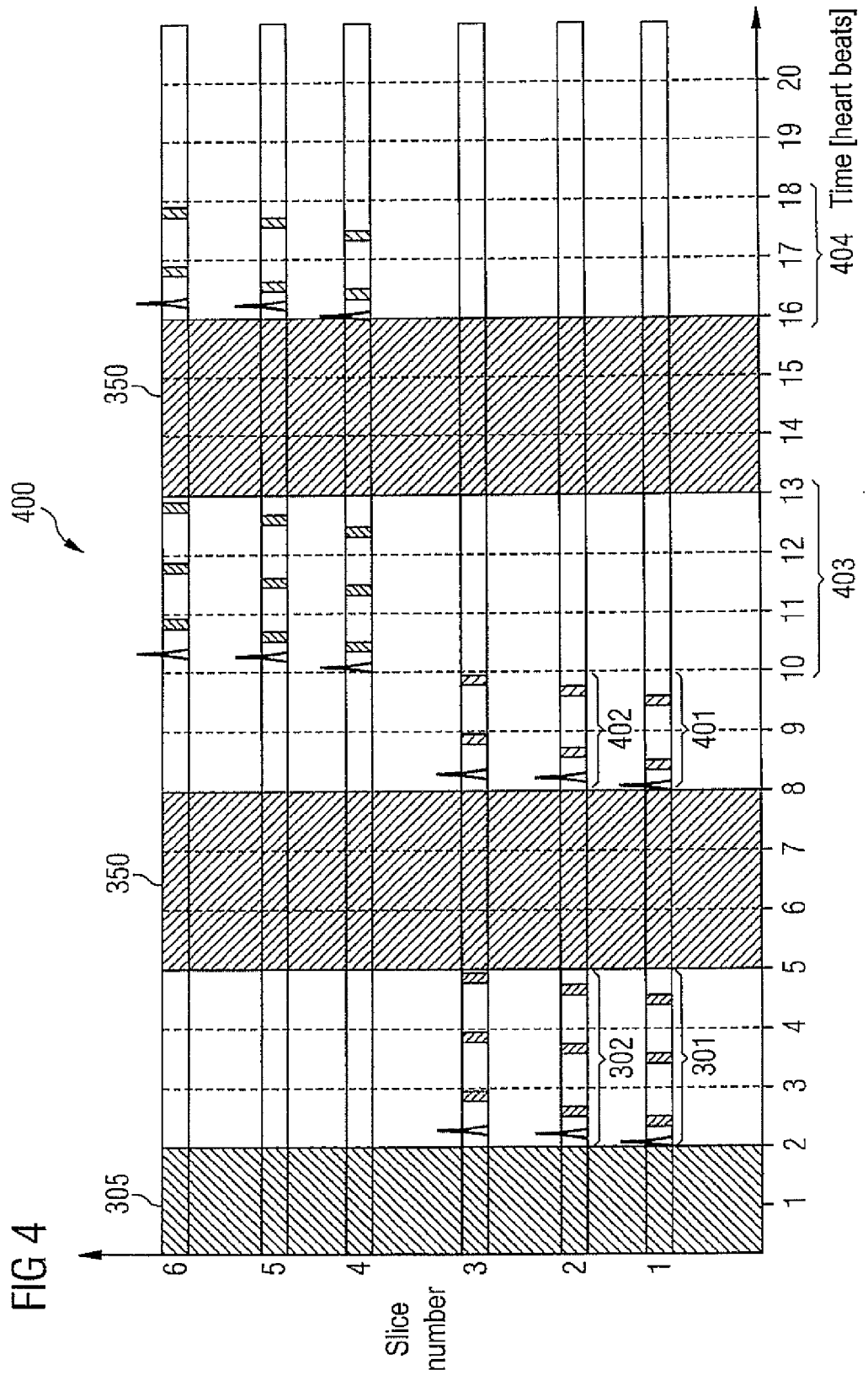
FIG. 4 schematically shows a sequence scheme according to a further embodiment of the present invention in which six slices are acquired during one breath hold phase, wherein three slices are respectively scanned in parallel.
Figure 5:
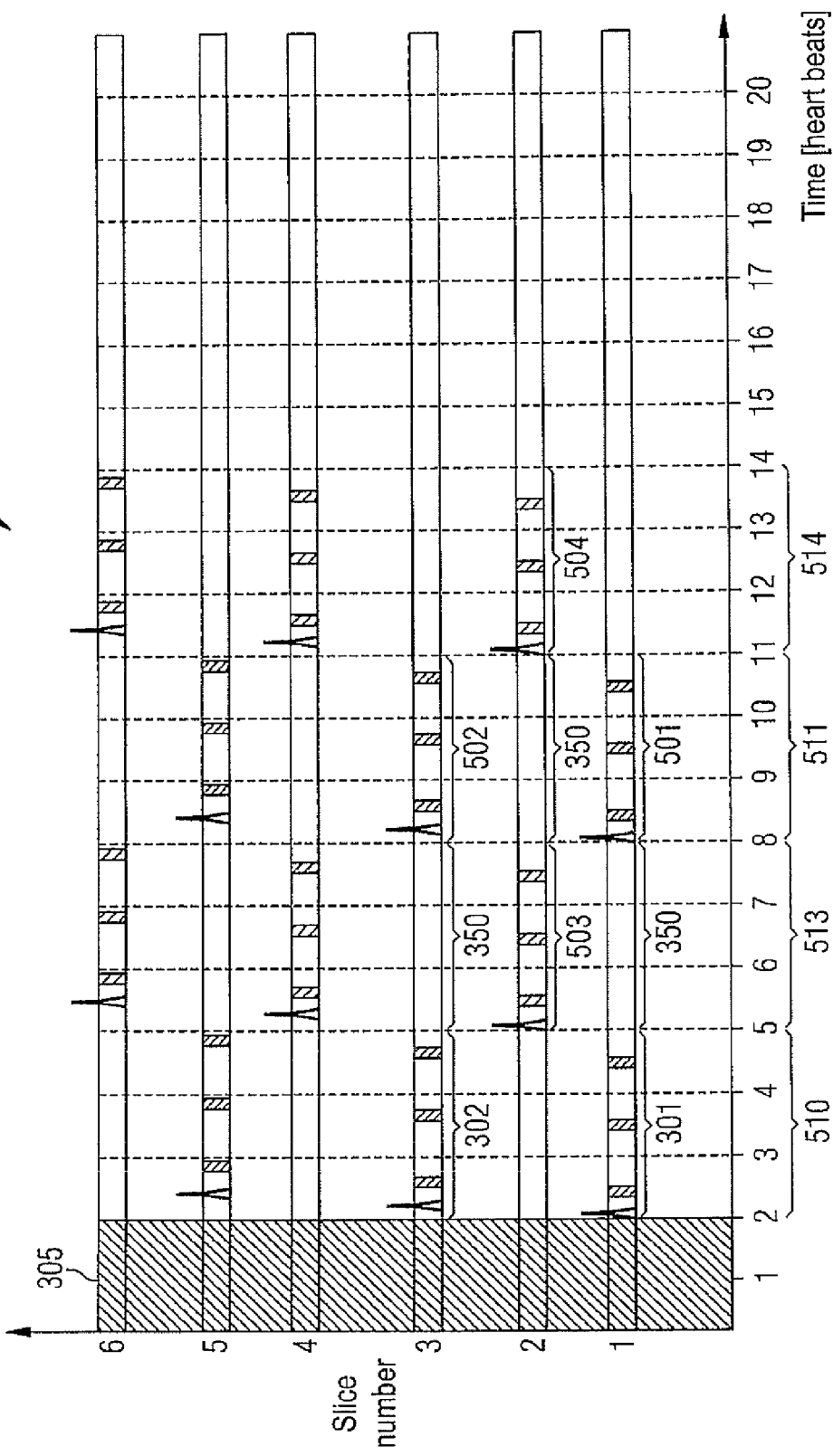
FIG. 5 schematically shows a sequence scheme according to a further embodiment of the present invention in which the scanning of six slices is interleaved during a breath hold phase.

FIG. 3 merely shows a possible sequence scheme 300 that can be used in the method of FIG. 2. Additional sequence schemes that implement at least two acquisition sequences in parallel are naturally similarly conceivable. FIG. 4 and FIG. 5 show two additional sequence schemes 400 and 500 that can be used in the method of FIG. 2.

The sequence scheme 400 of FIG. 4 comprises only two acquisition sequences for each slice to be scanned. The first acquisition sequence (for example 301 or 302) respectively comprises the inversion pulse and three readout steps, wherein the second acquisition sequence (for example 401 or 402) respectively possesses the inversion pulse and two readout steps. The scanning of a slice can be significantly accelerated via this abbreviation to five readout steps in total per slice. In spite of the abbreviation, five data points along the T1 decay curve continue to be provided to determine the T1 time constants. In spite of the acceleration, the T1 relaxation time can therefore be determined precisely. Together with the external reference scan 305, slices 1-3 can therefore be scanned within ten heart beats. The heart beats remaining within a breath hold phase can be utilized in order to scan additional slices 4-6 respectively in turn with groups of parallel acquisition sequence 403 and 404.

Within a group, the acquisition sequences are in turn slightly temporally offset so that the radiation of the inversion pulses and the implementation of the readout steps for different slices takes place in different cardiac phases, and therefore a mutual influencing due to temporal intersection is avoided. A recovery time period 350 (also called a recovery period or recovery heart beats) in which the steady state magnetization can be reestablished is respectively maintained between the acquisition sequences for a slice (for example 301 and 401). It is now likewise conceivable to implement the group of acquisition sequences 403 during the recovery periods 350 between the acquisition sequences for the first slices 1-3. The subsequent group of acquisition sequences 404 can be correspondingly implemented after the last acquisition sequences for the slices 1-3 and after a correspondingly long recovery period, thus in the present example after heart beat eleven (three recovery heart beats). The required duration for implementation of the sequence scheme 400 can therefore be additionally shortened.

In the present example, six slices can thus be scanned within 18 heart beats. This enables the quantification of the T1 relaxation times during only one breath hold phase within an already considerable volume.

An additional improvement can be achieved with the sequence scheme 500 shown in FIG. 5, in which the implementation of the acquisition schemes is interleaved. Each slice is thereby scanned with two acquisition schemes (sequences 301 and 501 for slice 1 or 302 and 502 for slice 3) that respectively in turn include an inversion pulse and three readout steps. A recovery period 350 is respectively provided after every acquisition sequence. The acquisition sequences of the groups 510 and 511 for the slices 1, 3 and 5 are in turn implemented in parallel with corresponding time offset. Slices 2, 4 and 6 are also scanned in parallel with the groups of acquisition sequences 513 and 514. The group of acquisition sequences 513 is implemented during the recovery period 350 between the groups 510 and 511. The acquisition sequences of the group 511 are correspondingly executed between the acquisition sequences of the groups 513 and 514. An optimal utilization of the limited available measurement time results via this interleaving since now MR data are also acquired during the recovery heart beats. Furthermore, the slices that are scanned in parallel exhibit a larger spatial interval due to the interleaving, such that the signals can accordingly be better separated.

A high precision in the determination of T1 can already be achieved with the use of six readout steps per slice. Since only 14 heart beats are required to acquire the data, the possibility naturally exists to implement additional readout steps to increase the precision for each slice. The sequence scheme 500 therefore enables a precise quantification of T1 in parallel for six slices within a time period of only 14 heart beats. An additional marked improvement is thus achieved relative to the acquisition schemes that were already shown. The interleaved acquisition can also be designated as an "interleaved" acquisition scheme.

The statements made in the preceding with reference to FIGS. 2 and 3 with regard to the acquisition sequences naturally reasonably apply to the sequence schemes shown in FIGS. 4 and 5. The parallel scanning of multiple slices during only one breath hold phase is achieved with all schemes. While conventional methods could quantify T1 for at most one slice during one breath hold phase, with the present method a quantification can take place for multiple slices in parallel, for example for six slices in the method according to FIGS. 4 and 5. Additional modifications of the sequence schemes are naturally similarly conceivable, for example a reduction of the number of readout steps given simultaneous interleaving of the acquisition sequences. An additional improvement of the method can be achieved by implementing the measurements at magnetic field strengths greater than 2.5 Tesla, for example at 3 Tesla. An increase of the signal-to-noise ratio of the acquired MR signals can therefore be achieved.

Figure 6:
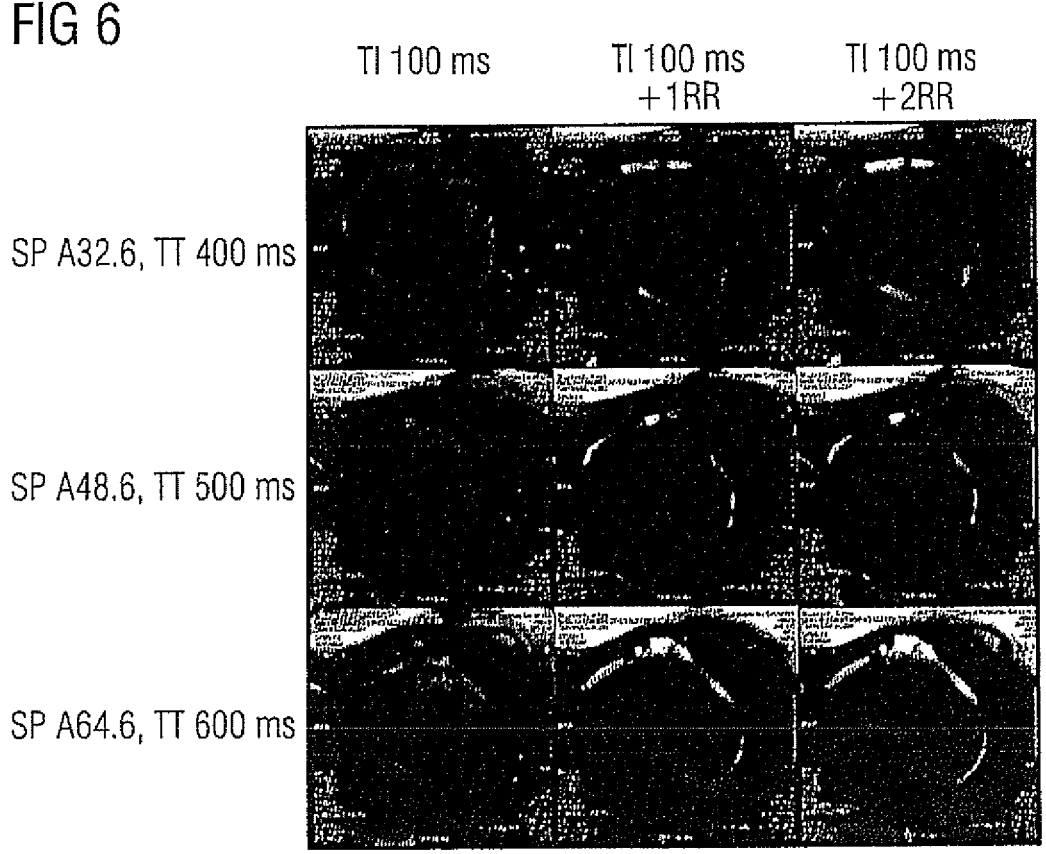
FIG. 6 shows an example of MR images that were acquired with an embodiment of the method according to the invention.

FIG. 6 shows an example of exposures of a heart of an examined person that were created with an embodiment of the method according to the invention. The rows thereby show respective images of the same slice, wherein each row was acquired with a different delay after a trigger event (Trigger Time TT=400 ms, 500 ms or, respectively, 600 ms). Each row thereby furthermore represents a different slice of the heart. Within a row, the MR images corresponding to different successive readout steps that were implemented following an inversion pulse with a specific inversion time of TI=100 ms. The slightly offset trigger points in time enable the interleaved measurement of all 3 slices in the same order of heart beats according to FIG. 5.

Significant advantages can be achieved with the method according to the invention relative to methods according to the prior art. Among these are the measurement of multiple slices within one heart beat with different effective inversion durations; the utilization of recovery periods via interleaved, parallel measurement of multiple slices; and the reduction of the measurement duration per readout slice via the use of external sensitivity information with a parallel imaging method. A large number of slices can be scanned within a single breath hold phase via the parallel measurement of multiple slices and the acceleration of the measurement. A volumetric, spatially resolved quantification of the T1 relaxation time can therefore be realized.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for magnetic resonance (MR) imaging, comprising the steps of:
   with a computerized control unit, operating an MR data acquisition device to implement at least one first acquisition sequence comprising a first acquisition sequence inversion pulse that excites nuclear spins in an examination subject and at least two successive first acquisition sequence read out steps in which MR data are acquired from a first slice of the examination subject, said MR data from said first slice representing T1 relaxation in said first slice following said excitation of nuclear spins by said first acquisition sequence inversion pulse;
   with said computerized control unit, operating said MR data acquisition device to implement at least one second acquisition sequence, which is temporally offset from and which at least partially temporally overlaps said first acquisition sequence, comprising a second acquisition sequence inversion pulse that excites nuclear spins in the examination subject and at least two successive second acquisition sequence readout steps in which MR data are acquired from a second slice of the examination subject, said MR data from said second slice representing T1 relaxation in said second slice following excitation of nuclear spins by said second acquisition sequence inversion pulse; and
   supplying said MR data from said first slice and said MR data from said second slice to a computerized processor and, in said computerized processor, generating a data file comprising said MR data from said first slice and said MR data from said second slice, as a data file in a form for electronic processing.

2. A method as claimed in claim 1 comprising emitting each of said first acquisition sequence inversion pulse and said second acquisition sequence inversion pulse as a slice-selective pulse.

3. A method as claimed in claim 1 comprising acquiring said MR data from said first slice in each of said at least two successive first acquisition sequence readout steps, and acquiring said MR data from said second slice in each of said at least two successive second acquisition sequence readout steps.

4. A method as claimed in claim 3 comprising, with said computerized control unit, operating said magnetic resonance data acquisition unit to implement each of said first acquisition sequence and said second acquisition sequence as a T1-weighted sequence wherein a T1 decay curve of magnetization excited by the respective first acquisition sequence inversion pulse and second acquisition sequence inversion pulse occurs, and wherein said at least two successive first acquisition sequence readout steps sample said decay curve in said first slice and wherein said at least two successive second acquisition sequence readout steps sample said decay curve in said second slice.

5. A method as claimed in claim 4 wherein said magnetization is a transverse magnetization, and comprising, with said computerized control unit, operating said MR data acquisition device to rephrase said transverse magnetization in said first acquisition sequence after each of said at least two successive first acquisition sequence readout steps, and, in said second acquisition sequence, to rephase said transverse magnetization after each of said at least two successive second acquisition sequence readout steps.

6. A method as claimed in claim 1 wherein each of said at least two successive first acquisition sequence readout steps and each of said at least two successive second acquisition sequence readout steps is a sequence selected from the group consisting of a True FISP sequence and a b-SSFP sequence.

7. A method as claimed in claim 1 comprising, with said computerized control unit, operating said MR data acquisition device to implement said first acquisition sequence and said second acquisition sequence as a parallel imaging procedure in which the MR data acquired by each of said at least two successive first acquisition sequence readout steps and said at least two successive second acquisition readout steps represent only a portion of k-space that is necessary for acquiring an entirety of an MR image of said first and second slices.

8. A method as claimed in claim 1 comprising, with said computerized control unit, operating said MR data acquisition unit to implement said first and second acquisition sequences with a temporal offset that causes said first acquisition sequence inversion pulse not to intersect with said second acquisition sequence inversion pulse and that causes none of said at least two successive first acquisition sequence readout steps to intersect with any of said at least two successive second acquisition readout steps.

9. A method as claimed in claim 8 comprising, with said computerized control unit, operating said MR data acquisition device to implement a third acquisition sequence, comprising a third acquisition sequence inversion pulse that excites nuclear spins in the examination subject and at least two successive third acquisition sequence readout steps in which MR data are acquired in a third slice of the examination subject, said MR data acquired from said third slice representing T1 relaxation in said third slice following excitation of nuclear spins by said third acquisition sequence inversion pulse and, with said computerized control unit, operating said MR data acquisition device to implement said first, second and third acquisition sequences with none of said first acquisition sequence inversion pulse, said second acquisition sequence inversion pulse and said third acquisition sequence inversion pulse overlapping, and with none of said at least two successive first acquisition readout steps, said at least two successive second acquisition readout steps, and said at least two successive third acquisition readout sequence inversion steps overlapping and, in said computerized processor, generating said data file from said MR data acquired from said first slice, said MR data acquired from said second slice and said MR data acquired from said third slice.

10. A method as claimed in claim 1 comprising, with said computerized control unit, operating said MR data acquisition device to implement a third acquisition sequence, comprising a third acquisition sequence inversion pulse that excites nuclear spins in the examination subject and at least two successive third acquisition sequence readout steps in which MR data are acquired in a third slice of the examination subject, said MR data acquired from said third slice representing T1 relaxation in said third slice following excitation of nuclear spins by said third acquisition sequence inversion pulse and, with said computerized control unit, operating said MR data acquisition device to implement said first, second and third acquisition sequences with none of said first acquisition sequence inversion pulse, said second acquisition sequence inversion pulse and said third acquisition sequence inversion pulse overlapping, and with none of said at least two successive first acquisition readout steps, said at least two successive second acquisition readout steps, and said at least two successive third acquisition readout sequence inversion steps overlapping and, in said computerized processor, generating said data file from MR data acquired from said first slice, said MR data acquired from said second slice and said MR data acquired from said third slice.

11. A method as claimed in claim 1 wherein the examination subject exhibits a heartbeat, and comprising acquiring an electronic signal representing the heartbeat of the examination subject and, with said computerized control unit, implementing each of said first acquisition sequence and said second acquisition sequence with triggering dependent on said heartbeat represented in said electronic signal.

12. A method as claimed in claim 11 wherein said heartbeat represented in said electronic signal defines respective phases of successive cardiac cycles, and comprising, with said computerized control unit, implementing each of said first acquisition sequence and said second acquisition sequence with triggering in a same phase of successive cardiac cycles.

13. A method as claimed in claim 11 wherein said heartbeat represented in said electronic signal defines respective cardiac phases in a cardiac cycle, and comprising, with said computerized control unit, triggering said first acquisition sequence inversion pulse and said second acquisition sequence inversion pulse to be emitted during different cardiac phases in a same cardiac cycle.

14. A method as claimed in claim 11 wherein said heartbeat represented in said electronic signal defines a cardiac cycle, and comprising, with said computerized control unit, implementing said first acquisition sequence and said second acquisition sequence during a same cardiac cycle.

15. A method as claimed in claim 11 wherein said heartbeat represented in said electronic signal defines different cardiac phases, and comprising, with said computerized control unit, triggering said at least two first acquisition sequence readout steps in a cardiac phase that is different from triggering of said at least two successive second acquisition sequence readout steps.

16. A method as claimed in claim 1 comprising, with said computerized control unit, operating said MR data acquisition unit to implement at least two first acquisition sequences to acquire MR data from said first slice, and to implement at least two second acquisition sequences to acquire MR data from said second slice, and wherein said computerized processor generates said data file from said MR data acquired during said at least two first acquisition sequences and said MR data acquired during said at least two second acquisition sequences.

17. A method as claimed in claim 16 wherein said first slice and said second slice are in a first group of slices of said examination subject, and wherein said computerized control unit operates said MR data acquisition device to implement said first acquisition sequence with a first acquisition sequence recovery period following thereupon, and to implement said second data acquisition sequence with a second acquisition sequence recovery. Following thereupon, and to implement at least one further acquisition sequence during at least one of said first acquisition sequence recovery period and said second acquisition sequence recovery period, said at least one further acquisition sequence comprising a further acquisition sequence inversion pulse and at least two further acquisition sequence readout steps in which MR data are acquired from a further slice of the examination subject outside of said first group, and wherein said computerized processor generates said data file from said MR data from said first acquisition sequence, said MR data from said second acquisition sequence, and said MR data from said further acquisition sequence.

18. A method as claimed in claim 17 wherein said further slice is in a second group of slices of the examination subject, and wherein said computerized control unit operates said MR data acquisition unit to implement a plurality of further acquisition sequences respectively for slices in said second group, during said recovery periods following said first and second acquisition sequences, and wherein said computerized processor generates said data file from MR data acquired from all slices in said first group and all slices in said second group.

19. A method as claimed in claim 1 wherein said computerized control unit operates said MR data acquisition unit to implement no more than two first acquisition sequences for said first slice and no more than two acquisition sequences for said second slice, and with said no more than two first acquisition sequences and said no more than two second acquisition sequences collectively comprising a total of no more than six readout steps.

20. A method as claimed in claim 1 wherein said computerized control unit operates said MR data acquisition device to implement said first acquisition sequence with an inversion time that is different from an inversion time for said second acquisition sequence.

21. A method as claimed in claim 1 comprising instructing said examination subject to execute a breath hold, and wherein said computerized control unit operates said MR data acquisition unit to implement said first acquisition sequence and said second acquisition sequence during said breath hold.

22. A method as claimed in claim 1 comprising, in said computerized processor, generating a T1 map from said data file comprising a quantitative, spatially resolved determination of a T1 decay time of said examination subject.

23. A method as claimed in claim 21 comprising, in said computerized processor, reconstructing an MR image from the MR data acquired in each of said readout steps, said MR image comprising a plurality of pixels and, for each pixel, said computerized processor determining a T1 relaxation time by implementing a statistical analysis of the MR data for that slice.

24. A magnetic resonance (MR) system, comprising:

an MR data acquisition device;

a computerized control unit, configured to operate said MR data acquisition device to implement at least one first acquisition sequence comprising a first acquisition sequence inversion pulse that excites nuclear spins in an examination subject and at least two successive first acquisition sequence read out steps in which MR data are acquired from a first slice of the examination subject, said MR data from said first slice representing T1 relaxation in said first slice following said excitation of nuclear spins by said first acquisition sequence in version pulse;

said computerized control unit being configured to operate said MR data acquisition device to implement at least one second acquisition sequence, which is temporally offset from and which at least partially temporally overlaps said first acquisition sequence, comprising a second acquisition sequence in version pulse that excites nuclear spins in the examination subject and at least two successive second acquisition sequence readout steps in which MR data are acquired from a second slice of the examination subject, said MR data from said second slice representing T1 relaxation in said second slice following excitation of nuclear spins by said second acquisition sequence in version pulse; and a computerized processor supplied with said MR data from said first slice and said MR data from said second slice, said computerized processor being configured to generate data file from said MR data from said first slice and said MR data from said second slice, in a form for electronic processing of said data file.

25. A magnetic resonance system as claimed in claim 24 wherein said computerized processor is configured to process said data file to generate a T1 map therefrom.

* * * * *